United States Patent [19]

Marshall, III

[11] Patent Number: 4,849,089
[45] Date of Patent: Jul. 18, 1989

[54] DISPOSABLE ELECTROMANIPULATION CHAMBER

[75] Inventor: John Marshall, III, Boulder, Colo.

[73] Assignee: Electropore, Inc., Boulder, Colo.

[21] Appl. No.: 313,169

[22] Filed: Feb. 21, 1989

Related U.S. Application Data

[63] Continuation-in-part of Ser. No. 283,215, Dec. 12, 1988, which is a continuation-in-part of Ser. No. 47,208, May 8, 1987, which is a continuation-in-part of Ser. No. 861,534, May 9, 1986, abandoned.

[51] Int. Cl.$^4$ .................. C12N 13/00; C12N 15/00
[52] U.S. Cl. .................. 204/299 R; 204/183.1; 204/180.1; 935/52; 935/85; 935/93; 435/287; 435/173; 435/172.2; 435/172.3
[58] Field of Search ............ 204/299 R, 183.1, 180.1; 435/287, 289, 173, 172.2, 172.1, 172.3; 935/52, 53, 93, 89

[56] References Cited

U.S. PATENT DOCUMENTS 3,095,359  6/1963  Heller ..................... 195/78
4,634,665  1/1987  Axel et al. ............... 435/68

FOREIGN PATENT DOCUMENTS

WPB01J/24-
76 404  9/1984  German Democratic Rep. .

OTHER PUBLICATIONS

"Introduction and Expression of DNA Molecules in Eukaryotic Cells by Electroporation"—Andreason & Evans, BioTechniques—vol. 6, No. 7 (1988).
"Hemolysis of Human Erythrocytes by a Transient Electric Field"—Kinosita and Tsong—Proc. Natl. Acad. Sc. U.S.A., vol. 74, No. 5, pp. 1923–1927, May 1977, Biochemistry.

*Primary Examiner*—John F. Niebling
*Assistant Examiner*—John S. Starsiak, Jr.
*Attorney, Agent, or Firm*—Dorr, Carson, Sloan & Peterson

[57] ABSTRACT

An electromanipulation chamber for selectively holding a suspension of vesicles is disclosed having a one-piece holder molded from dielectric material wherein the holder comprises an outer cylindrically-shaped collar and an inner circular-shaped ring having a formed annular region centrally located therein. A passageway is formed through the ring and the collar and a pair of electrodes having a diameter slightly greater than the inner diameter of the collar is mounted on opposing sides of the annular region. The pair of electrodes and the annular region form the electromanipulation chamber and a positive fluid-tight seal is formed aournd the edges of the annular region with electrodes to contain the suspension with the vesicles.

24 Claims, 2 Drawing Sheets

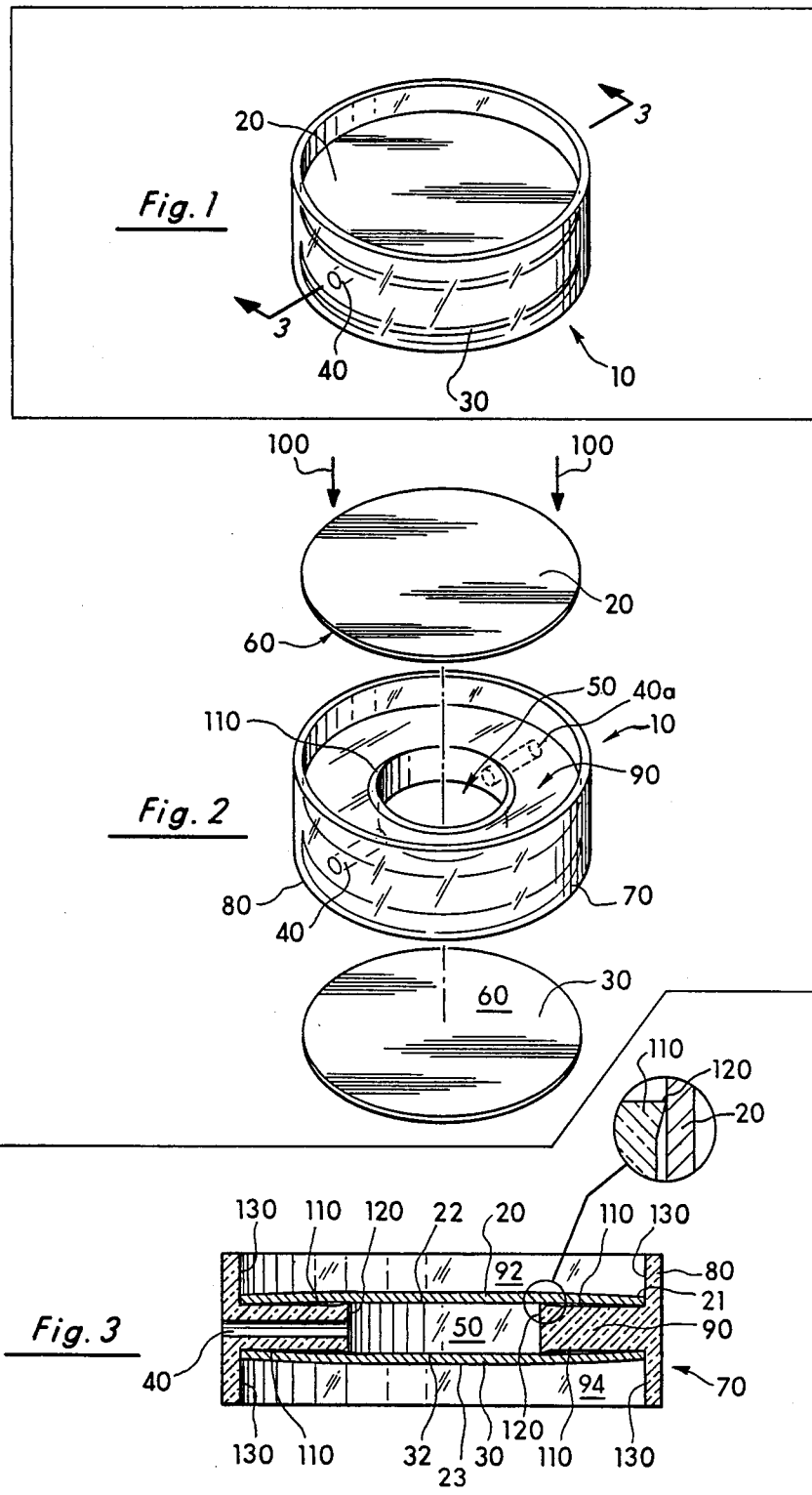

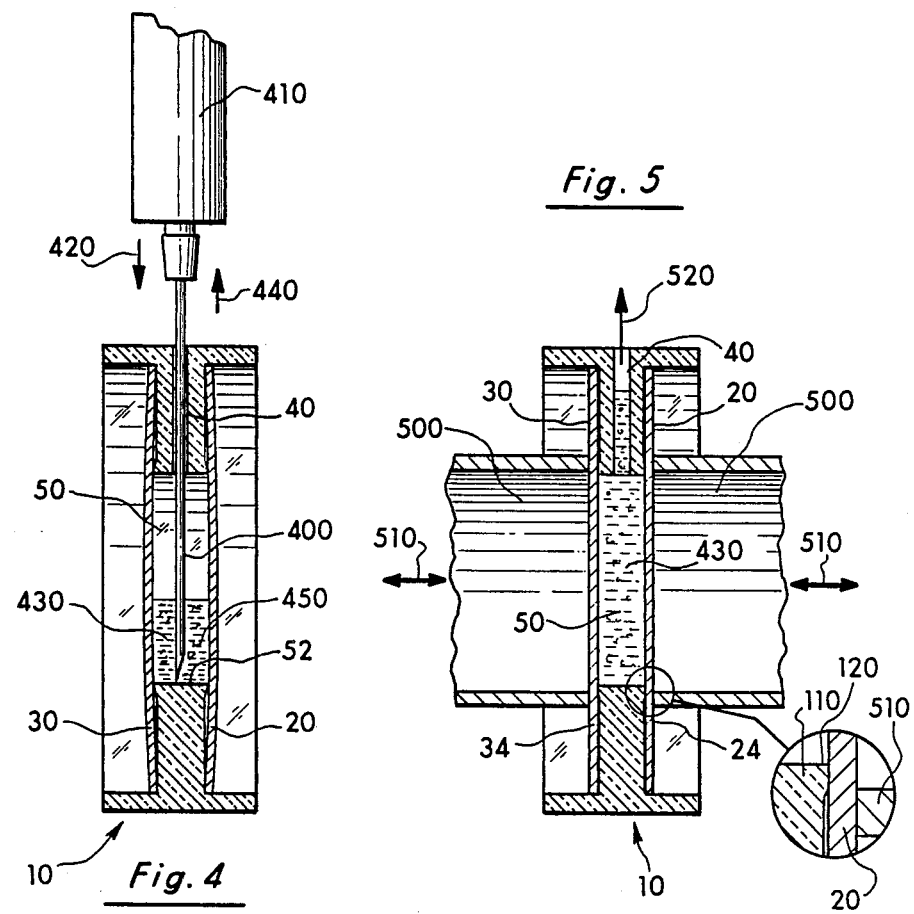
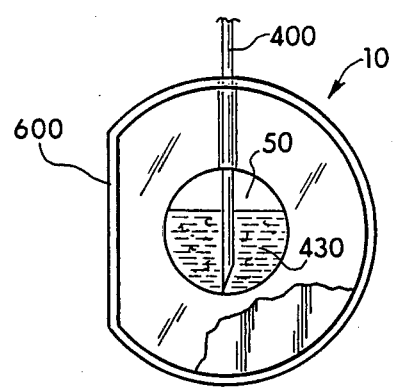
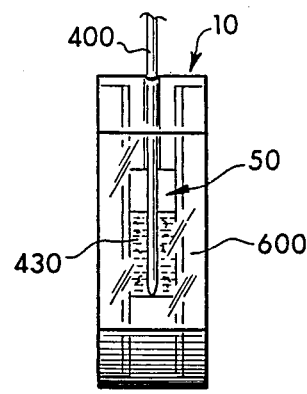

DISPOSABLE ELECTROMANIPULATION CHAMBER

BACKGROUND OF THE INVENTION

1. Related Applications

This is a continuation-in-part of application Ser. No. 07/283,215 filed Dec. 12, 1988, now pending, entitled "Improved Impedance Matching for Cell Membrane Alteration Instrumentation" which is a continuation-in-part of application Ser. No. 07/047,208, filed May 8, 1987, now pending, entitled "High Speed, High Power Apparatus for Vesicle Prealignment, Poration, Loading and fusion in Uniform Electric Fields and Method Therefor" which is a continuation-in-part of Ser. No. 06/861,534, filed May 9, 1986, now abandoned.

2. Field of the Invention

The present invention is related to a chamber for the electromanipulation of vesicles in liquid suspension. Vesicle is herein defined as a body which resembles a bladder especially in constituting a small thin-walled cavity such as (a) a plant or animal structure (e.g., a cyst, vacuole, or cell) or (b) a non-biological structure (e.g., as a liposome or microsphere) having the general form of a membranous cavity such as a thin sac and especially when filled with fluid. Cells are generally defined as microscopic masses of protoplasm bounded externally by a semi-permeable membrane. More particularly, this invention relates to the electromanipulation of vesicles in a uniform electric field produced by a disposable apparatus having a chamber formed between two parallel plate electrodes and a dielectric holder.

Statement of the Problem

It is well known that vesicular structures can be altered through the application of electric fields (i.e., electroporation). For example, electroporation is a type of electromanipulation of a biological membrane such that a style of permeability is induced in the membrane which acts like small holes or "pores." This process establishes a semi-stable membrane state such that molecules and macromolecules may cross the otherwise impermeable membrane barrier. This semistable state may be reversed and repaired upon warming the membrane in question. If stored at low temperatures, however, the semi-stable membrane state can exist for hours or days. Electroporation has been successfully utilized to create semi-stable membrane states in a number of different cell types such as cultured cell lines, mammalian primary cell cultures, mammalian and embryonic stem cells, isolated intracellular vesicles, dicot and monocot plant protoplasts, protists and bacteria. Electroporation has been used to introduce DNA molecules, to load cells with dyes and other molecules, and to extract molecules from cells without requiring cell lysis. See "Introduction and Expression of DNA Molecules in Eukaryotic Cells by Electroporation", Volume 6, No. 7, BIOTECHNIQUES (1988), Page 6750. The use of electric fields to transfer biological macromolecules such as genetic material (DNA), RNA, and protein into cells is well know. Another form of electromanipulation is fusion. Fusion is defined as the merger or coalescence of at least two vesicles to form a single vesicular entity.

The prior approach of Heller as set forth in U.S. Pat. No. 3,095,359 shows the use of a reaction chamber having an open top formed within a rectangular vessel preferably of glass or other high dielectric material. The electrodes of Heller are flat metal plates mounted on the outside of the vessel and out of direct contact with the material in the chamber being treated. The volume of the chamber shown in Heller is not disclosed. Both Stolley (German Democratic Republic Pat. No. WP B 01 J/2476 404, Sept. 12, 1984) and Kinosita & Tsong ("Hemolysis of Human Erythrocytes by a Transient Electric Field, Proc. Natl. Acad. Sc. USA, Vol. 74, No. 5, pp. 1923-1927, May 1977, Biochemistry) discuss the use of parallel electrodes. Stolley discloses the use of two plate electrodes arranged parallel to each other in a container holding vesicles but no specific structure is shown. Kinosita and Tsong illustrate the use of a cylindrical cavity enclosed by a pair of stainless steel electrodes and a plexiglass cell.

In "Introduction and Expression of DNA Molecules in Eukaryotic Cells by Electroporation+, by Andreason and Evans, 650 Biotechniques, Volume 6, No. 7 (1988) the authors disclose a rectangular reusable parallel stainless steel electromanipulation chamber utilizing disposable one milliliter spectrophotometer curvettes.

A need exists in the field of treating solutions containing particles, vesicles and cells for a disposable chamber capable of treating large volumes of solutions such as one milliliter or greater.

Solution to the Problem

The present invention is also discussed in the Andreason, et al. article and provides a solution to the problem in the industry stated above of providing a fully disposable chamber capable of holding large quantities such as 1.0 milliliters of suspension. The suspension carrying the vesicles is selectively inserted and removed through a small hole in the side of the chamber.

SUMMARY OF THE INVENTION

The electromanipulation chamber of the present invention comprises a central holder having a cylindrically shaped collar with an integral centrally disposed ring. The ring has a central cavity which defines the sides of the chamber. The collar and the ring are made from a dielectric material which is nonbinding to protein. A ridge is formed around the cavity on each of the upper and lower surfaces of the ring. A hole is formed through the collar and the ring to provide a fluid pathway from the cavity to the atmosphere. A pair of disk-shaped electrodes press-fittingly engage the opposite ends of the collar and engage the formed ridge on each side of the ring to form a fluid seal. The electrodes define the top of the fluid-tight chamber. Each of the electrodes are comprised of conductive material coated with an inert noble metal.

DESCRIPTION OF THE DRAWING

FIG. 1 is a perspective view of the electromanipulation chamber of the present invention;

FIG. 2 is an exploded perspective view showing the components of the electromanipulation chamber of FIG. 1;

FIG. 3 is a cross-sectional view through the center of the chamber of FIG. 1;

FIG. 4 is an illustration showing a syringe injecting a solution into the electromanipulation chamber of FIG. 1 viewed in cross-section;

FIG. 5 is a cross-sectional illustration of the electromanipulation chamber of FIG. 1 mounted in a fixture to discharge electrodes;

FIG. 6 is a second embodiment of the present invention making use of an optical viewing window; and FIG. 7 is a side view of the alternate embodiment of the FIG. 6.

DETAILED DESCRIPTION OF THE PRESENT INVENTION

In FIG. 1 the electromanipulation chamber 10 of the present invention is shown. The chamber 10 has two opposing electrodes 20 and 30 and a small formed hole 40. As shown in FIG. 2, the chamber 10 has a formed annular region or cavity 50 which comprises the sides of the electromanipulation chamber as will be discussed.

1. Electrodes—In FIG. 2, each of the electrodes 20 and 30 are identical and are formed of conductive material such as copper, brass, or steel. Each electrode 20 and 30 is plated on all sides with an inert noble metal such as gold or platinum so as not to react chemically with the solution before, during, or after electromanipulation. Each electrode is formed in the shape of a thin disk having a diameter of about 2⅜ inches and a thickness of about 1/16 inch.

It is to be expressly understood that different conductive metals, plating material, geometric shapes other than circular (such as square) and dimensions could be utilized under the teachings of the present invention for different suspensions and applications.

2. Holder—The chamber 10 also incorporates a holder 70 which comprises an outer cylindrically-shaped collar 80 and an inner circular ring 90. The outer edge of the ring 90 is integral, in the preferred embodiment with the central area of the inside surface of the collar 80 and is made from a one-piece polycarbonate material or from any suitable dielectric material which is non-binding with protein such as plastic, ceramic, or glass. The ring 90 splits the collar 80 into upper and lower regions 92 and 94 which are substantially equal in volume. The cavity 50 has a diameter of about ⅝ inch and a height of about ⅛ inches to obtain a volume of at least 1 ml.

Under the teachings of the present invention, the holder 70 may be of one piece construction or with the ring 90 and collar 80 separately manufactured and connected together. The upper and lower regions 92 and 94 may in certain applications be of unequal volume, the volume of the cavity 50 may be varied to meet design requirements, and different geometric shapes other than cylindrical may be utilized.

3. Chamber 50—Each electrode 20, 30 is designed, as shown in FIG. 3, to press-fittingly engage the inner surface 100 of the collar 80 as the electrode is pushed with a suitable tool, not shown, in the direction of arrows 100 causing the edge of the collar to move slightly outward. The diameter of each electrode is slightly greater than the inside diameter of the collar 80 such as by 0.002 inch. When press-fittingly engaged with the holder 70, the electrodes 20, 30 abut the formed V-shaped ridge 110 outer surfaces 110 of the ring 90 and press-fittingly engage the inner surface of the collar at the juncture of the ring. The electrodes 20, 30, as shown in FIG. 3, are spherically deformed with the edges 21 being held lower by the inner surfaces 130 of the collar 80 than the center 23 of the electrodes which abut the ridges 110. Ridges 110 are each circular in shape and comprise a right triangle shaped configuration having a height of about 0.015 inches and a base about 0.100 inches. The knife edge 120 abuts against the electrode 20, 30. This forms an electromanipulation chamber 50 between the inner surfaces 22 and 32 of electrodes 20 and 30 respectively and the inner surface 120 of the ring 90 defining a volume of at least 1 ml. Hence, vesicles, can now be suspended in a solution inserted in cavity 50. The electrodes engage the edges 120 under tension due to the aforesaid spherical deformation thereby creating a fluid-tight seal.

It is to be expressly understood that the use of a ridge of triangular cross-section represents a preferred approach to sealing the chamber 50 and that other suitable cross-sections and approaches could be utilized to achieve the desired fluid-tight seal.

4. Insertion of Suspension—In FIG. 3, a passageway or hole 40 is formed through the collar 80 and the ring 90 to provide access by means of a needle 400 connected to a syringe 410 as shown in FIG. 4 to the cavity 50.

In FIG. 4, a syringe 410 bearing a solution 430 such as HEPES buffered saline is injected into the cavity 50. The solution 430 contains the vesicles (illustrated as 450) which are to be electrically treated. In a preferred use, the chamber 10 is held vertically, as shown, and the needle 400 is inserted until it hits the end 52 of the cavity 50 opposing the hole 40. The solution 430 is carefully injected into the cavity to avoid the creation of bubbles in the solution. The operator can observe the insertion through the transparent sides of the holder 70. If bubbles are present when in solution 430 when electromanipulation occurs substantial damage could result or inaccurate electromanipulation could be obtained due to the electric field distortions caused by the bubbles. After injection, the needle 400 is removed.

In FIGS. 6 and 7 an alternative embodiment shows the use of a flat optical viewing port 600 to better view the operation of fluid injection. In the embodiment of FIG. 1, the plastic of the holder 70 is sufficiently optically transparent to view the injection, but the use of a flat surface 600 enhances the viewing.

5. Electromanipulation—In FIG. 5, the chamber 10 is vertically mounted between two ring-shaped discharge electrodes or electrical contacts 500 and 510 which selectively engage or disengage the chamber by moving the contacts in the direction of arrows 510. The discharge contacts 500 firmly engage the electrodes 20, 30 with sufficient force to deform the knife edge 120 of the ridge 110 by partially flattening the knife edge. This also causes some of the solution to move upwardly through the hole 40 which pushes out any remaining bubbles of air in the solution 430. When the contacts 500 properly engage the outer surfaces 24, 34 of electrdes 20, 30, an electromanipulation pulse or pulses are applied to the chamber 50. Treatment of the vesicles now occurs. It is to be noted that the size of the formed hole 40 is such that the solution, because of the surface tension of the solution, does not normally leave the chamber 50 except as described above.

After treatment, the suspension 430 can be removed by means of the syringe 410 and needle 400 as shown in FIG. 4 by withdrawing the solution in the direction of arrow 440 through the needle 400. The needle 400 is inserted until it hits the opposing wall. After use, the cylinder may be disposed of.

6. Summary—What has been set forth in FIGS. 1 through 5 is a disposable electromanipulation chamber that utilizes a pair of opposing electrodes 20 and 30 mounted in a holder above an electromanipulation chamber. The chamber is low cost in manufacture in that the holder 70 can be quickly manufactured from a single-piece polycarbonate material. The hole 40 can be drilled and then the parallel opposing plates 20 and 30 can be inserted. The upstanding collar 80 forms a guide for positioning the plates 20 and 30 above the inner ring 90 as well as providing a convenient lip 130 for the upper and lower regions for holding and carrying the chamber 10 by the user. In addition, the raised collar on both sides of the chamber serves the function of guiding the discharge electrodes 500 in their engagement onto the outer surfaces of the electrodes 20 and 30. In the preferred embodiment, the ring-shaped discharge electrodes are greater in diameter than the diameter of the electromanipulation chamber 50.

Finally, as shown in FIG. 3, the chamber 10 is symmetrical above and below the formed hole 40 which is designed to access the electromanipulation chamber at its center.

The chamber of the present invention is designed as a non-flow through chamber. However, it is expressly understood that a second formed hole 40a in the inner ring 1290 opposing the first hole 1240 could be inserted and that fluid could be pumped into and out from the chamber.

While preferred embodiments of the present invention have been shown, it is to be expressly understood that modifications and changes may be made thereto and that the present invention is set forth in the following claims.

I CLAIM:

1. An apparatus having an electromanipulation chamber selectively holding a suspension, said apparatus comprising:
   a holder comprising:
   (a) an outer collar,
   (b) an inner ring having a formed annular region centrally located therein, said ring dividing said collar into upper and lower regions,
   (c) a passageway formed through of said ring and said collar,
   a pair of thin electrodes made from conductive material having a diameter slightly greater that the inner diameter of said collar, each said electrode press-fittingly engaging one of said upper or lower regions, the outer edge of each said electrode press-fittingly engaging the inner surface of said collar at the junction of said ring with said collar,
   means on the outer surface of said ring for providing a fluid-tight seal between each of said electrodes and said ring, and
   said pair of electrodes and said annular region of said ring forming said chamber, said formed passageway providing means for the delivery of said suspension into and out from said chamber, said diameter of said passageway being small enough so that the surface tension of said suspension prevents the flow of said suspension from said chamber.

2. The apparatus of claim 1 wherein said collar extends above said engaged electrodes to provide a lip around said upper and lower regions.

3. The apparatus of claim 1 wherein said holder is of one-piece cylindrical construction and is made from dielectric material which is nonbinding to protein.

4. The apparatus of claim 1 wherein said holder is made from optically transparent material for viewing the insertion of said suspension into said chamber.

5. The apparatus of claim 4 wherein one side of said collar is formed with a flat surface in order to provide a viewing port for said chamber.

6. The apparatus of claim 1 wherein said electrodes are circular disks plated with an inert noble metal.

7. The apparatus of claim 1 wherein said providing means are opposing formed circular ridges.

8. The apparatus of claim 1 wherein said apparatus further comprises a pair of opposing electrical contacts selectively abutting the outer surfaces of said electrodes with sufficient force to push a portion of said suspension in said chamber into said passageway in order to remove any air bubbles in said chamber.

9. The apparatus of claim 8 wherein each said electrical contact is ring-shaped with a diameter greater than the diameter of said chamber.

10. An apparatus having an electromanipulation chamber selectively holding a suspension, said apparatus comprising:
    a holder molded from dielectric material, said holder comprising:
    (a) an outer cylindrically-shaped collar,
    (b) an inner circular-shaped ring having a formed annular region centrally located therein, said ring dividing said collar into upper and lower regions, said ring having its outer edge engaging the inside surface of said collar, said ring further having a pair of opposing formed circular ridges on the upper and lower edges of said annular region,
    (c) a passageway formed through of said ring and said collar,
    a pair of electrodes made from conductive material having a diameter slightly greater that the inner diameter of said collar, each said electrode press-fittingly engaging one of said upper or lower regions, the outer circular edge of each said electrode press-fittingly engaging the inner surface of said collar at the junction of said ring with said collar and abutting said ridge of said ring so that said each said electrode is spherically deformed, and
    said pair of electrodes and said formed annular region forming said chamber, said formed passageway providing means for the delivery of said suspension into and out from said chamber, said diameter of said passageway being small enough so that the surface tension of said suspension prevents the flow of said suspension from said chamber.

11. An apparatus having an electromanipulation chamber selectively holding a suspension, said electromanipulation chamber comprising:
    a one-piece holder molded from dielectric material, said holder comprising:
    (a) an outer cylindrically-shaped collar,
    (b) an inner circular-shaped ring having a formed annular region centrally located therein, said ring dividing said collar into upper and lower regions, said ring having its outer edge integral with the inside surface of said collar,
    (c) a passageway formed through said ring and said collar,
    a pair of electrodes made from conductive material having a diameter slightly greater that the inner diameter of said collar, each said electrode press-fittingly engaging one of said upper or lower regions, the outer circular edge of each said electrode press-fittingly engaging the inner surface of said collar at the junction of said ring with said collar, and
    said pair of electrodes and said formed annular region forming said chamber, said formed passageway providing means for the delivery of said suspension into and out from said chamber, said diameter of said passageway being small enough so that the surface tension of said suspension prevents the flow of said suspension from said chamber.

12. An apparatus having an electromanipulation chamber selectively holding a suspension, said electromanipulation chamber comprising:
a one-piece holder molded from dielectric material, said holder comprising:
(a) an outer cylindrically-shaped collar,
(b) an inner circular-shaped ring having a formed annular region centrally located therein, said ring dividing said collar into upper and lower regions, said ring having its outer edge integral with the inside surface of said collar, said ring further having a pair of opposing formed circular ridges on the upper and lower edges of said annular region, each of said ridges terminating in a knife edge,
(c) a passageway formed through said ring and said collar,
a pair of electrodes made from conductive material having a diameter slightly greater that the inner diameter of said collar, each said electrode press-fittingly engaging one of said upper or lower regions, the outer circular edge of each said electrode press-fittingly engaging the inner surface of said collar at the junction of said ring with said collar and abutting said circular knife edge of said ring so that said each said electrode is spherically deformed, and
said pair of electrodes and said formed annular region forming said chamber, said formed passageway providing means for the delivery of said suspension into and out from said chamber, said diameter of said passageway being small enough so that the surface tension of said suspension prevents the flow of said suspension from said chamber.

13. The apparatus of claim 12 wherein said knife edge of said ridge further deforms under force applied to said electrodes during said electromanipulation in order to remove any air bubbles in said suspension out through said passageway.

14. A system having an electromanipulation chamber selectively holding a suspension and electrical contacts for applying electromanipulation pulses, said electromanipulation chamber comprising:
a one-piece holder molded from dielectric material which is nonbinding with protein, said holder comprising:
(a) an outer cylindrically-shaped collar,
(b) an inner circular-shaped ring having a formed annular region centrally located therein, said ring dividing said collar into equal upper and lower regions, said ring having its outer edge integral with the central area of the inside surface of said collar, said ring further having a pair of opposing formed circular ridges on the upper and lower edges of said annular region, each of said ridges being substantially triangular in cross-section and terminating in a knife edge,
(c) a passageway formed through the center of said ring and said collar, said passageway lying in a plane parallel to said ring,
a pair of electrodes made from conductive material having a diameter slightly greater that the inner diameter of said collar, each of said electrodes being plated with an inert noble metal and formed in the shape of a disk, each said electrode press-fittingly engaging one of said upper or lower regions, the outer circular edge of each said electrode press-fittingly engaging the inner surface of said collar at the junction of said ring with said collar and abutting said circular knife edge of said ring so that said each said electrode is spherically deformed, and
said electrical contacts abutting the outer surfaces of said electrodes with aforesaid force, and said pair of electrodes and said formed annular region forming said chamber, said formed passageway providing means for the delivery of said suspension into and out from said chamber, said diameter of said passageway being large enough to receive a syringe needle but small enough so that the surface tension of said suspension prevents the flow of said suspension from said chamber.

15. The system of claim 14 wherein each of said electrical contact are ring-shaped with a diameter greater than the diameter of said annular region.

16. A method for electromanipulation of vesicles suspended in a solution, said method comprising the steps of:
inserting the needle of the syringe containing said solution into a passageway formed in an electromanipulation chamber,
said chamber having a pair of opposing conductive electrodes over a cavity formed from dielectric material, delivering said solution from said syringe into said chamber,
removing said needle of said syringe from said chamber,
applying electrical contacts to the outer surface of said opposing electrodes with sufficient force to provide a fluid seal between said electrodes and said cavity,
electro-pulsing the electrical contacts and electrodes in order to electromanipulation the vesicles in said solution contained in said cavity,
removing said electrical contacts from said electrodes,
inserting said needle of said syringe in said formed passageway of said chamber and removing said solution from said chamber, and
removing said needle of said syringe from said chamber.

17. The method of claim 16 wherein the steps of inserting said needle into said chamber occurs with said needle being inserted into said chamber until the end of said needle hits the inner wall of said chamber.

18. The method of claim 16 wherein the step of applying said electrical contacts further includes the step of removing air bubbles from said chamber by forcing said solution from said chamber into said formed passageway.

19. An electromanipulation chamber comprising:
a central holder made from transparent dielectric material, said central holder comprising:
a. a collar,
b. a ring centrally disposed in said collar, said ring having a centrally located formed cavity, said cavity being at least 1 ml in volume,
c. a ridge formed around said cavity on each of the upper and lower surfaces of said ring, each said ridge being located at the edge of said ring at said cavity, and
d. a passageway formed through said collar and said ring, said passageway extending from the outer surface of said collar to said cavity, a pair of electrodes, said electrodes press-fittingly engaging opposing ends of said collar, each of said electrodes abutting the ridge on said ring closest to said electrode in order to seal said cavity thereby making said cavity fluid tight.

20. The electromanipulation chamber of claim 19 in which said ring is integral with said collar.

21. The electromanipulation chamber of claim 19 wherein said ring is composed of polycarbonate.

22. The electromanipulation chamber of claim 19 wherein said ring is composed of material which is non-binding to protein.

23. The electromanipulation chamber of claim 19 wherein said electrodes are composed of a conductive material coated with an inert noble metal.

24. The electromanipulation chamber of claim 19 wherein said collar is cylindrically-shaped, said ring is circular, and said electrodes are each formed in the shape of a thin disc.

* * * * *